ent Number: 4,909,963
Date of Patent: Mar. 20, 1990

United States Patent [19]
Kwak et al.

[54] PHOTOCHROMIC ARTICLE

[75] Inventors: Won S. Kwak, Akron, Ohio; Chin-Wen Chen, Mission Viejo, Calif.

[73] Assignee: PPG Industries, Inc., Pittsburgh, Pa.

[21] Appl. No.: 280,604

[22] Filed: Dec. 6, 1988

Related U.S. Application Data

[60] Division of Ser. No. 74,692, Jul. 23, 1987, Pat. No. 4,816,584, which is a continuation-in-part of Ser. No. 929,936, Nov. 12, 1986, abandoned, which is a continuation-in-part of Ser. No. 912,718, Sep. 15, 1986, abandoned.

[51] Int. Cl.$^4$ .............................................. G02B 5/23
[52] U.S. Cl. .................................... 252/586; 252/589; 252/600; 544/71; 350/354
[58] Field of Search ....................... 252/582, 589, 586; 544/70, 71; 350/354

[56] References Cited

U.S. PATENT DOCUMENTS

| | | | |
|---|---|---|---|
| 3,407,145 | 10/1968 | Brule | 350/354 X |
| 3,562,172 | 2/1972 | Ono et al. | 252/300 |
| 3,578,602 | 5/1971 | Ono et al. | 252/300 |
| 3,843,550 | 10/1974 | Hinnen | 252/586 |
| 3,980,480 | 9/1976 | Laridon | 430/345 X |
| 4,215,010 | 7/1980 | Hovey et al. | 252/300 |
| 4,289,497 | 9/1981 | Hovey | 350/354 X |
| 4,342,668 | 8/1982 | Hovey et al. | 252/586 |
| 4,440,672 | 4/1984 | Chu | 252/586 |
| 4,634,767 | 1/1987 | Hoelscher et al. | 544/71 |
| 4,636,561 | 1/1987 | Hosoda | 544/71 |
| 4,637,698 | 1/1987 | Kwak et al. | 351/163 |

FOREIGN PATENT DOCUMENTS

| | | |
|---|---|---|
| 1927849 | 12/1970 | Fed. Rep. of Germany . |
| 238611 | 8/1986 | German Democratic Rep. . |
| 48-23787 | 3/1973 | Japan . |
| 1227713 | 4/1971 | United Kingdom . |
| 1243370 | 8/1971 | United Kingdom . |
| 2174711A | 1/1986 | United Kingdom . |

OTHER PUBLICATIONS

Arnold et al, Tetrachedron, 27(1971), pp. 1699–1713, "Spektroskopische strukturuntersuchunger . . .".
Balli et al, Chemical Abstracts, 95:80769g (1981).
Techniques of Chemistry, vol. III, Photochromism, G. H. Brown, Ed., Chapter 3 by Robert C. Bertelson, pp. 44–49, 54, 92, and 415, Wiley-Interscience, New York (1971).
Organic Synthesis, Collective Volume I, Henry Gilman, Ed., John Wiley and Sons, Inc., N.Y., 1932, pp. 411–412.
"A New Chemical Reaction with the Nitrosyl Radical NOH", O. Baudisch, Science, vol. 92, pp. 336–337 (1940).
"Preparation of o-Nitrosophenols from Benzene or Other Aromatic Hydrocarbons at Room Temperature", O. Baudisch, J. Amer. Chem. Soc., 63, 622 (1941).
"o-Nitrosophenols I.", G. Cronheim, J. Org. Chem., 12, pp. 1–7 (1947).
"o-Nitrosophenols II.", G. Cronheim, J. Org. Chem., 12, pp. 7, 14, 17–18 (1947).

Primary Examiner—Teddy S. Gron
Assistant Examiner—Richard Trenor
Attorney, Agent, or Firm—Irwin M. Stein

[57] ABSTRACT

Described are photochromic spiro(indoline)benzoxazine compounds having substituents on the benzoxazine portion of the compound, and their use in plastic hosts to impart a photochromic response thereto.

20 Claims, No Drawings

PHOTOCHROMIC ARTICLE

CROSS REFERENCE TO RELATED APPLICATIONS

This application is a division of application Ser. No. 74,692, filed Jul. 23, 1987, now U.S. Pat. No. 4,816,584, which in turn is a continuation-in-part application of our application Ser. No. 929,936, filed Nov. 12, 1986, now abandoned, which is in turn a continuation-in-part application of our application Ser. No. 912,718, filed Sept. 15, 1986, now abandoned.

DESCRIPTION OF THE INVENTION

The present invention relates to novel photochromic compounds, and to compositions and articles containing such photochromic compounds. Photochromism is a reversible phenomenon illustrated by a compound which, when exposed to the radiation of light involving ultraviolet rays, such as sunlight or the light of a mercury lamp, changes color and then returns to its original color if the radiation is discontinued or the compound is stored in the dark. A compound illustrating this property is called a "photochromic compound".

Various types of photochromic compounds have been synthesized and suggested for use in applications in which a color change or darkening is induced by sunlight. In particular, spiro(indoline) naphthoxazine compounds, as described in U.S. Pat. Nos. 3,562,172, 3,578,602, 4,215,010, and 4,342,668, show particular advantages for sunglasses and ophthalmic lenses. Such photochromic compounds either in crystalline form or in solution or dispersion in a transparent medium change rapidly from a colorless state to blue when exposed to sunlight or ultraviolet radiation and return to the original colorless state by being allowed to stand in the dark or in the absence of strong ultraviolet radiation.

DETAILED DESCRIPTION OF THE INVENTION

In accordance with the present invention, there are provided novel substituted spiro(indoline) benzoxazine photochromic compounds represented by the following graphic formula I,

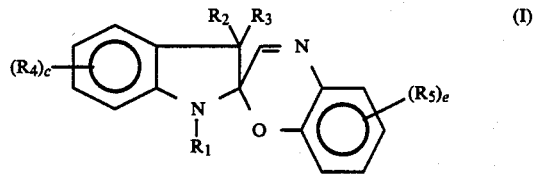

In the above graphic formula I, $R_1$ is selected from the group consisting of $C_1-C_8$ alkyl, e.g., methyl, ethyl, propyl, butyl, etc., phenyl, phen($C_1-C_4$)alkyl, e.g., benzyl, naphth ($C_1-C_4$) alkyl, e.g., 1-naphthylmethyl, allyl, acrylyl, methacrylyl, carboxy ($C_2-C_6$) alkyl, e.g., β-carboxyethyl, Y-carboxypropyl and δ-carboxybutyl, cyano ($C_2-C_6$) alkyl, e.g., β-cyanoethyl, Y-cyanopropyl, β-cyanoisopropyl, and δ-cyanobutyl, $C_1-C_4$ acyloxy ($C_2-C_6$) alkyl, i.e., [$R_cC(O)R_d$—, wherein $R_c$ is a $C_1-C_4$ alkyl and $R_d$ is a $C_2-C_6$ alkyl], e.g., acetoxyethyl, acetoxypropyl, propionyloxyethyl, acetoxybutyl, and propionyloxypropyl, hydroxy ($C_2-C_6$) alkyl, e.g., hydroxyethyl, hydroxypropyl and hydroxybutyl, $(C_2H_4O)_m \cdot CH_3$, wherein m is a number of from 1 to 6, and mono- and di-substituted phenyl, said phenyl substituents being selected from $C_1-C_4$ alkyl and $C_1-C_5$ alkoxy, e.g. methoxy, ethoxy, propoxy, butoxy and pentoxy. Preferably, $R_1$ is selected from the group consisting of $C_1-C_4$ alkyl, phenyl, benzyl, 1-naphth($C_1-C_2$) alkyl, such as 1-naphthylmethyl, carboxy($C_2-C_4$) alkyl, cyano ($C_2-C_4$) alkyl, $C_1-C_4$ acyloxy ($C_2-C_4$) alkyl, e.g., $C_1-C_4$ acyloxyethyl, hydroxy ($C_2-C_4$) alkyl and $(C_2H_4O)_m CH_3$ wherein m is a number of from 1 to 3, e.g., 2.

$R_2$ and $R_3$ of formula I are each selected from the group consisting of $C_1-C_5$ alkyl, phenyl, mono- and di-substituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1-C_4$ alkyl and $C_1-C_5$ alkoxy radicals. More particularly, $R_2$ and $R_3$ are each selected from $C_1-C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

$R_4$ in graphic formula I is selected from the group consisting of $C_1-C_5$ alkyl, halogen, e.g., chloro and fluoro, $C_1-C_5$ alkoxy, nitro, cyano, $C_1-C_4$ monohaloalkyl, e.g., chloromethyl, fluoromethyl, chloroethyl, chloropropyl, etc., $C_1-C_4$ polyhaloalkyl, e.g., trihaloalkyl, $C_1-C_8$ alkoxycarbonyl, and $C_1-C_4$ acyloxy, i.e., $R_cC(O)$—, wherein $R_c$ is a $C_1-C_4$ alkyl, such as acetoxy. While any halogen, i.e., chlorine, bromine, iodine and fluorine, may be used in respect to the aforesaid halogen or haloalkyl substituents, chlorine, fluorine and bromine, especially chlorine and fluorine is preferred for the halogen substituent and fluorine is preferred for the polyhaloalkyl substituent, e.g., trifluoromethyl ($CF_3$). Preferably, $R_4$ is selected from the group consisting of $C_1-C_2$ alkyl, chlorine, fluorine, $C_1-C_2$ trihaloalkyl, e.g., trihalomethyl such as trifluoromethyl, and $C_1-C_5$ alkoxy.

The letter "c" in formula I is a number from 0 to 4, e.g., 0 to 2, such as 1 or 2. When "c" is 2 or more, the $R_4$ substituents may be the same or different and in either case are selected from the aforedescribed group. The $R_4$ substituent(s) may be located on any of the available carbon atoms of the indolino portion of the compound, i.e., at the 4', 5', 6', or 7' positions. When "c" is 2, the $R_4$ substituents can be present at the 4' and 5', 5' and 6', 4' and 7' or 6' and 7' carbon atoms of the indolino moiety.

It is possible that the photochromic organic material of graphic formula I can be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "c" is one, the photochromic compound may be substituted at the 4' position on the indoline ring, at the 6' position of that ring or comprise a mixture of such isomers. When "c" is two, the photochromic compound may be substituted at any combination of the 4', 5', 6', or 7' carbon atoms of the indoline ring (as heretofore indicated) and may comprise an isomeric mixture of such compounds, e.g., a mixture of compounds having substituents at the 4' and 5', 4' and 6', 5' and 6', 4' and 7', 5' and 7', and 6' and 7' positions of the indoline ring. Commonly, when "c" is 2 the substituents are located at the 4' and 5', or 5' and 6' positions. Also contemplated are materials containing mixtures of such isomers, e.g., materials comprising 4' (and 6') 5'-substituted spiro indoline benzoxazines.

$R_5$ in graphic formula I is selected from the group consisting of halogen, e.g., chloro, fluoro, or bromo, $C_1$–$C_4$ alkyl, $C_1$–$C_5$ alkoxy, nitro, cyano, thiocyano, $C_1$–$C_4$ monohaloalkyl, e.g., chloromethyl and chloroethyl, $C_1$–$C_2$ polyhaloalkyl, e.g., trihaloalkyl, such as trifluoromethyl and 1,1,1-trifluoroethyl. The letter "e" in formula I is a number of from 1 to 4, usually, 1, 2, or 3, and preferably 1–2. In particular, $R_5$ is $C_1$–$C_2$ alkyl, $C_1$–$C_2$ alkoxy, chloro, bromo, nitro, or trifluoromethyl.

The $R_5$ substituent(s), i.e., when "e" is 1, may be located on any of the available carbon atoms of the benzene ring of the benzoxazine moiety of the compound, i.e., at the 5, 6, 7 or 8 positions. Preferably, the $R_5$ substituent is present on the 5, 6, or 7 carbon atoms of the benzene ring of the benzoxazine moiety. When "e" is 2 or more, the $R_5$ substituents may be the same or different and in either case are selected from the above-described group. When "e" is 2, the $R_5$ substituents may be located at the 5 and 7 or 6 and 8 positions. When "e" is 3, the $R_5$ substituents may be located at the 5, 6, and 7; 5, 7, and 8; 6, 7, and 8; or 5, 6, and 8 positions.

Of particular interest, are photochromic materials represented by graphic formula I wherein $R_1$ is a $C_1$–$C_4$ alkyl, such as methyl, ethyl, n-propyl, isopropyl, n-butyl, secondary butyl, isobutyl and tertiary butyl; $R_2$ and $R_3$ are each methyl, ethyl or phenyl; $R_4$ is selected from trifluoromethyl, chlorine, fluorine, methyl or methoxy; $R_5$ is selected from methoxy, methyl, nitro, fluoro, bromo or chloro, "c" is 1 or 2, and "e" is 1 or 2.

Examples of contemplated compounds within the scope of graphic formula I are listed in Table I. The prime (') designations for the $R_4$ substituent positions in Table I have been omitted. Compound 1 may be named: 7-methoxy-1',3',3', 4'(and 6'), 5'-pentamethylspiro[2H-1,4-benzoxazine-2,2'-indoline]. Compounds 2–48 may be similarly named as substituted spiro(indoline) benzoxazines using the substituents described in Table I for such compounds. In naming the spiro(indoline)benzoxazines, the IUPAC rules of organic nomenclature have been used. The positions on the indoline portion of the molecule have been numbered counterclockwise starting with the nitrogen atom as number one (1), and are identified by a prime number, e.g., 3'. The positions on the benzoxazine portion of the molecule have been numbered clockwise starting with the oxygen atom as number one (1).

TABLE I

| Compound No. | $R_1$ | $R_2$ | $R_3$ | $R_4$ | $R_4$ | $R_5$ | $R_5$ |
|---|---|---|---|---|---|---|---|
| 1 | Me | Me | Me | 4(6)-Me | 5-Me | 7-OMe | — |
| 2 | Me | Me | Me | 4(6)-Me | 5-Me | 7-OMe | 5-OMe |
| 3 | Me | Me | Me | 5-OMe | — | 7-OMe | 5-OMe |
| 4 | Me | Me | Me | 4(6)-Me | 5-Me | 7-OMe | 5-Cl |
| 5 | Me | Me | Me | 4(6)-Me | 5-Me | 6-NO$_2$ | — |
| 6 | Me | Me | Me | 4(6)-Me | 5-Me | 6-Cl | — |
| 7 | Me | Me | Ph | — | — | 7-OMe | — |
| 8 | Me | Me | Et | — | — | 7-OMe | 5-OMe |
| 9 | n-Bu | Me | Me | — | — | 7-OMe | 5-OMe |
| 10 | Me | Cyclohexyl | — | — | — | 7-OMe | 5-OMe |
| 11 | Me | Me | Me | 5-OMe | — | 6-NO$_2$ | — |
| 12 | Me | Me | Me | 5-OMe | — | 6-NO$_2$ | 8-OMe |
| 13 | Et | Me | Me | 5-OMe | — | 6-NO$_2$ | 8-OMe |
| 14 | Me | Me | Et | 4(6)-Me | 5-Me | 6-NO$_2$ | 8-OMe |
| 15 | Me | Me | Ph | — | — | 6-NO$_2$ | 8-OMe |
| 16 | Me | Me | Me | 4(6)-Me | 5-Me | 8-NO$_2$ | 6-OMe |
| 17 | Me | Me | Me | — | — | 8-NO$_2$ | 6-OMe |
| 18 | Me | Me | Me | 5-OMe | — | 8-NO$_2$ | 6-OMe |
| 19 | Et | Me | Me | — | — | 7-OMe | 6-Br |
| 20 | Me | Me | Et | 4(6)-Me | 5-Me | 7-OMe | 5-Me |
| 21 | i-Pr | Me | Me | 5-OMe | — | 7-OMe | 5-OMe |
| 22 | Benzyl | Me | Me | — | — | 7-NO$_2$ | — |
| 23 | Me | Me | Me | 4(6)-F | — | 7-OMe | 5-OMe |
| 24 | Me | Me | Me | 6-Cl | — | 7-OMe | 5-OMe |
| 25 | Me | Me | Me | 7-F | — | 7-OMe | 5-OMe |
| 26 | Me | Me | Me | 7-Cl | — | 7-OMe | 5-OMe |
| 27 | Me | Me | Me | 7-Br | — | 7-OMe | 5-OMe |
| 28 | Me | Me | Me | 5-F | — | 7-OMe | 5-OMe |
| 29 | Me | Me | Me | 5-Cl | — | 7-OMe | 5-OMe |
| 30 | Me | Me | Me | 5-OMe | — | 7-OMe | 5-OMe |
| 31 | Me | Me | Me | 5-OMe | — | 7-OMe | — |
| 32 | Me | Me | Me | 6-CF$_3$ | — | 7-OMe | 5-OMe |
| 33 | Me | Me | Et | 4(6)-F | — | 7-OMe | 5-OMe |
| 34 | Me | Me | Me | 4(6)AcO | — | 7-OMe | 5-OMe |
| 35 | Me | Me | Me | 4(6)CF$_3$ | — | 7-OMe | 5-OMe |
| 36 | Me | Me | Me | 4(6)F | 5-F | 7-OMe | 5-OMe |
| 37 | Me | Me | Me | 4(6)Cl | 5-Cl | 7-OMe | 5-OMe |
| 38 | Me | Me | Me | 4(6)F | — | 7-OMe | 5-Cl |
| 39 | Me | Me | Me | 4(6)F | — | 7-OMe | 5-F |
| 40 | Me | Me | Me | 4(6)AcO | — | 7-OMe | 5-OMe |
| 41 | Me | Me | Me | — | 5-AcO | 7-OMe | 5-OMe |
| 42 | Me | Me | Me | 4(6)AcO | 5-F | 7-OMe | 5-OMe |
| 43 | Me | Me | Me | 4(6)AcO | 5-Cl | 7-OMe | 5-OMe |
| 44 | CNPr | Me | Me | — | — | 7-OMe | — |
| 45 | HOC(o)Et | Me | Me | — | — | 7-OMe | 5-OMe |

TABLE I-continued

| Compound No. | SUBSTITUENT | | | | | | |
|---|---|---|---|---|---|---|---|
| | R₁ | R₂ | R₃ | R₄ | R₄ | R₅ | R₅ |
| 46 | (EtO)₂Me | Me | Me | — | — | 7-OMe | — |
| 47 | HOEt | Me | Me | — | — | 7-OMe | — |

Key:
Me = methyl
n-Bu = n-butyl
Et = ethyl
i-Pr = isopropyl
CNPr = γ-cyanopropyl
(EtO)₂Me = CH₃OCH₂CH₂OCH₂CH₂
Ph = phenyl
OMe = methoxy
NO₂ = nitro
HOC(o)Et = β-carboxyethyl
Br = bromine
Cl = chlorine
F = fluorine
AcO = acetoxy
HOEt = hydroxyethyl The photochromic materials of the present invention can be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine, and ethylene glycol. The compounds can also be dispersed in liquids containing water, alcohols and other solvents.

The photochromic materials of the present invention can also be dissolved in colorless or transparent solutions prepared from transparent polymers (or copolymers) or blends of such transparent polymers and a suitable organic solvent, e.g., polymers of transparent host materials described hereinafter dissolved in one or more of the aforesaid described organic solvents. Examples of such solutions include a polyvinylacetateacetone solution, a nitrocellulose-acetonitrile solution, a polyvinylchloride-methylethylketone solution, a polymethylmethacrylate-acetone solution, a cellulose acetate-dimethylformamide solution, a polyvinylpyrrolidone-acetonitrile solution, a polystyrene-benzene solution, and an ethyl cellulose-methylene chloride solution.

The aforesaid photochromic solutions or compositions can be applied to a transparent support, such as cellulose triacetate, polyethylene terephthalate or baryta paper and dried to obtain a photochromic material, which may be color formed by ultraviolet radiation and returned to colorless by removing the source of ultraviolet radiation.

The photochromic materials of the present invention or compositions containing same can be applied to or incorporated within a coating or article of polymerized organic material, i.e., a synthetic plastic host material. Preferably, the host material article is a solid transparent or an optically clear material, e.g., materials suitable for ophthalmic elements, such as ophthalmic lenses, or materials useful for applications such as windows, windshields, etc. A host material containing the photochromic compounds of the present invention can be used in the preparation of photochromic plastic films, sheets and lenses, such as lenses for sunglasses, ski goggles, visors, camera lenses and variable density filters. As used herein, the term "optical element" is meant to include lenses and transparencies. The photochromic materials of the present invention may be incorporated into coatings such as paints, inks, etc. by admixing the material with the fluid coating composition before it is applied to the host surface and dried.

Examples of host materials which can be used with the photochromic compounds of the present invention include: polymers, i.e., homopolymers and copolymers, of polyol(allyl carbonate) monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, polyethyleneterephthalate, polystyrene, poly(styrene-methylmethacrylate) copolymers, poly(styrene-acrylonitrile) copolymer, and polyvinylbutyral. Transparent copolymers and blends of the transparent polymers are also suitable as host materials. Preferably, the host material is an optically clear polymerized organic material prepared from a polycarbonate, such as poly(4,4'-dioxydiphenol-2,2-propane), which is sold under the trademark, LEXAN; a polymethylmethacrylate, such as the material sold under the trademark, PLEXIGLAS; polymerizates of a polyol(allyl carbonate), especially diethylene glycol bis(allyl carbonate), which is sold under the trademark, CR-39, and its copolymers with for example vinyl acetate, e.g., copolymers of from 80–90 percent diethylene glycol bis(allyl carbonate) and 10–20 percent vinyl acetate; particularly 80–85 percent of the bis(allyl carbonate) and 15–20 percent vinyl acetate, cellulose acetate, cellulose propionate, cellulose butyrate, polystyrene and its copolymers with methyl methacrylate, vinyl acetate and acrylonitrile, and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

The polyol (allyl carbonate) monomers can be represented by the graphic formula:

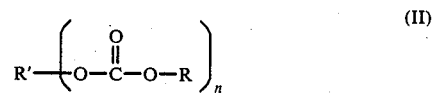

(II)

wherein R is the radical derived from an unsaturated alcohol and is commonly an allyl or substituted allyl group, R' is the radical derived from the polyol, and n is a whole number from 2-5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

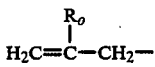

wherein $R_o$ is hydrogen, halogen, or a $C_1$-$C_4$ alkyl group. Specific examples of R include the groups: allyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly, R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

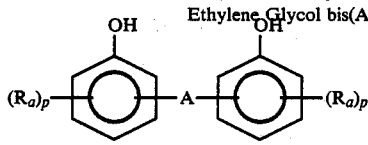

(III)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), Ra represents lower alkyl substituents of from 1 to 3 carbon atoms, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-$, and $-CH_2CH_2CH_2-O-CH_2CH_2CH_2-$; alkylene polyether groups such as $-CH_2CH_2-O-CH_2CH_2-O-CH_2CH_2-$ and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene bis(para-phenyl), i.e.,

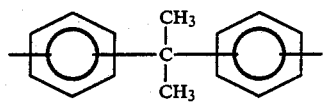

IV

Most commonly, R' is $-CH_2CH_2-$, $-CH_2CH_2-O-CH_2CH_2-$, or $-CH_2CH_2-O-CH_2CH_2-O-CH_2CH_2-$.

Specific examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which can be utilized in the invention herein contemplated are:

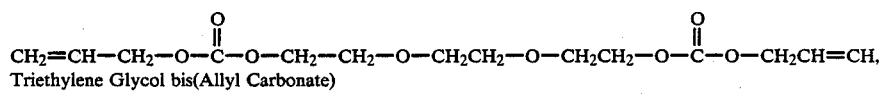

Triethylene Glycol bis(Allyl Carbonate)

V

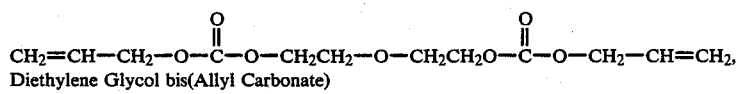

Diethylene Glycol bis(Allyl Carbonate)

VI and

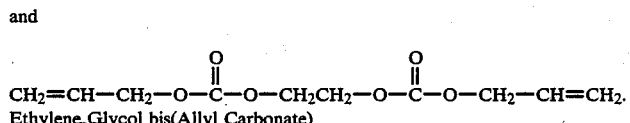

Ethylene Glycol bis(Allyl Carbonate)

VII

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

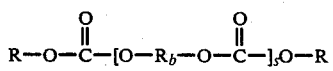

VIII wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula,

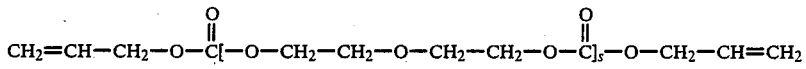

IX wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer can be used. In that embodiment, the monomer is thickened by heating or partially polymerized by using small, e.g., 0.5-1.5 parts of initiator per hundred parts of monomer (phm) to provide a nongel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

The amount of the photochromic compound or composition-containing same applied to or incorporated into a host material is not critical and depends generally upon the intensity of the color of the composition desired upon irradiation thereof and upon the method used to incorporate or apply the photochromic compound. Typically, the more compound added, the greater the color intensity. Generally such amount can be described as a photochromic amount. Usually, the amount of photochromic compound incorporated into the host material ranges from about 0.01 to about 20 percent by weight, more usually from about 0.05 to about 10 percent by weight, based on the weight of the host material. Stated another way, the amount of photochromic compound used to impart a photochromic effect will typically vary from about 1 to about 50, e.g., 1 to 10 milligrams of the photochromic compound per square inch of the surface of the host material independent of the thickness of the host material article. Hence, the photochromic compound is present in a higher concentration in thin samples, films, or coatings, and in a lower concentration in thick samples.

Solutions of the photochromic compounds of the present invention undergo a change in color upon exposure to ultraviolet radiation and return to their original color or colorless state upon removal of the source of ultraviolet radiation. Such color change may be repeated numerous times.

The photochromic compounds or compositions of the present invention can be applied to or incorporated into a host material by methods known in the art. Such methods include dissolving or dispersing the compound in the host material, i.e., imbibation of the photochromic compound in the host material, by immersion, thermal transfer, or coating, and incorporation of the photochromic compound as part of a separate layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds or compositions of the present invention can be mixed with a polymerizable composition that, upon curing, produces an optically clear polymeric host material and the polymerizable composition cast as a film, sheet or lens, or injection molded or otherwise formed into a sheet or lens;

(b) The photochromic compounds of the present invention can be dissolved or dispersed in water, alcohol or other solvents or solvent mixtures and then imbibed into the solid host material by immersion for from several minutes to several hours, e.g., 2-3 minutes to 2-3 hours of the host material in a bath of such solution or dispersion. The bath is conventionally at an elevated temperature, usually in the range of 50°-120° C. Thereafter, the host material is removed from the bath and dried;

(c) The photochromic compounds and compositions may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, e.g., in an oven, for from a minute to several hours at temperatures in the range of from 80°-180° C.;

(d) In a variation of the above imbibation procedure, the photochromic compound or composition can be deposited onto a temporary support, e.g., a sheet of kraft paper, aluminum foil, polymer film or fabric, which is then placed in contact with the host material and heated, e.g., in an oven;

(e) The photochromic compounds can be dissolved or dispersed in a transparent polymeric material which can be applied to the surface of the host in the form of an adherent film by any suitable technique such as spraying, brushing, spin-coating or dip-coating; and (f) Finally, the photochromic compounds can be incorporated or applied to a transparent polymeric material by any of the above-mentioned methods, which can then be placed within the host material as a discrete layer intermediate to adjacent layers of a host material(s).

The photochromic materials of the present invention may be synthesized by reaction of the corresponding $R_5$-substituted nitroso-phenol compound with the corresponding $R_4$-substituted indoline (Fischer's base) or indolium salt, e.g., the iodide salt, compound. The two precursor materials are reacted in substantially stoichiometric amounts in a suitable solvent, such as toluene or ethanol, containing a base, such as triethylamine or piperidine, at temperatures of from about 40° C. to about 120° C. or 140° C. until the reaction is completed.

Any common organic solvent (polar and non-polar) except for aliphatic hydrocarbon solvents, such as hexane, may be used as the reaction medium. Contemplated as suitable solvents are alcohols such as $C_1$-$C_4$ alkanols, e.g., methanol, ethanol, isopropanol, and the butanols; aromatic solvents such as benzene, toluene and xylene; ketones such as acetone, methyl ethyl ketone and methyl isobutyl ketone; esters such as ethyl acetate; chlorinated lower aliphatic hydrocarbons such as methylene chloride and chloroform; dimethylsulfoxide, dimethylformamide and tetrahydrofuran.

While reaction temperatures below 40° C. may be used, the reaction rate is very slow and commercially unacceptable. Reaction temperatures above 120° C. may cause decomposition of the product. Hence, temperatures of from 40° C. to 120° C., e.g., 50° C. to 100° C. are contemplated. Stirring of the reaction medium at elevated reaction temperatures within the aforesaid ranges is recommended to prevent decomposition of the benzoxazine product.

Any organic or inorganic base may be used to react with the hydrogen halide that is liberated during the reaction as a result of using the indolium halide salt. Amines such as trimethylamine, triethylamine, diisopropylamine, piperidine, pyridine and piperazine may be used. Inorganic basic reagents such as sodium carbonate, sodium bicarbonate, potassium hydroxide, sodium hydroxide and sodium acetate may be used. The use of inorganic reagents will entail a two-phase reaction medium, i.e., an inorganic and organic phase. The basic reagent is commonly used in a stoichiometric excess, although stoichiometric amounts may be used.

The photochromic material is recovered from the reaction mixture, e.g., by filtration or decanting—depending on whether the product is a solid or liquid. The product may be purified by flash column chromatography, crystallization, boiling with carbon black or other techniques known in the art.

More particularly, the photochromic compounds of the present invention may be prepared by reacting one equivalent of the corresponding substituted Fischer's base iodo salt with one equivalent of the corresponding substituted nitrosophenol in an ethanol solution containing an excess of diisopropylamine. The liquid reaction mixture is heated to 70° C. and maintained at about that temperature for about 5 hours. The progress of the reaction may be monitored by thin layer chromatography (TLC). The ethanol solvent and excess diisopropylamine are evaporated and the residue diluted with hexane to produce a reaction slurry. The solid in the slurry is recovered by filtration, washed with 10% sodium hydroxide, e.g., three times, dried over magnesium sulfate and filtered through a pad of silica gel. The resulting crude product is purified by column chromatography using ethylacetate and hexane as eluents.

Still more particularly, one equivalent of 2-nitroso-5-methoxyphenol may be condensed with an equivalent of 1,2,3,3,4,5(or 5,6)-hexamethyl indolium iodide. A suspension of the iodide salt and the 2-nitroso-5-methoxyphenol in ethanol may be refluxed in the presence of an excess of piperidine until the condensation reaction has been completed, e.g., 2 to 5 hours. The resulting spiro-(indoline) benzoxazine is compound 1 in Table I.

The photochromic compounds of the present invention may also be prepared by condensing the corresponding indoline (Fischer's base) or indolium salt, e.g., a halide such as the iodide salt, compound with a metal chelate of the corresponding $R_5$-substituted nitrosophenol compound. This process is described in copending U.S. patent application Ser. No. 912,717 filed Sept. 26, 1986 for Method for Synthesizing SpiroOxazines.

In the aforedescribed application, a metal salt, e.g., a nitrate, sulfate or chloride salt of the metals copper, cobalt, nickel, iron, chromium, zinc, silver, palladium, mercury, gold, titanium, manganese, cadmium, platinum, zirconium, lanthanum, cerium, aluminum, lead or tin, is reacted with the $R_5$-substituted nitrosophenol in the presence of nitrous acid. The nitrous acid may be generated in situ by the combination of sodium nitrite and a weak acid such as acetic acid. This reaction may be conducted in water or a water-glacial acetic acid mixture at a pH in the range of 2-5. The resulting metal chelate compound, i.e., the metal chelate of the $R_5$-substituted-nitrosophenol, may be condensed (usually using stoichiometric amounts) with the corresponding Fischer's base in a substantially non-reactive organic medium, e.g., toluene or ethanol. Generally, this condensation reaction occurs in from about 0.1-4 hours at temperatures from 40° C.-140° C., more usually near the reflux temperature of the organic medium. Separation and purification of the final product may be accomplished by crystallization using a solvent, such as hexane, that is capable of dissolving the spiro-benzoxazine compound.

The present invention is more particularly described in the following examples which are intended as illustrative only since numerous modifications and variations therein will be apparent to those skilled in the art.

EXAMPLE 1

To a 3-necked 500 milliliter flask fitted with condenser, dropping funnel and thermometer was charged 31.03 grams (0.25 mole) of m-methoxyphenol, 17.25 grams (0.25 mole) sodium nitrite and 10.0 grams (0.25 mole) of sodium hydroxide. The mixture was cooled in an ice bath to about 3° C. and sufficient water added to give a final volume of about 300 milliliters. 31.87 grams (0.325 mole) of sulfuric acid was slowly added to the cooled mixture at a rate such that the temperature of the contents in the reaction flask did not exceed 6° C. After all of the sulfuric acid had been completely charged, the flask and ice bath were shaken. This resulted in an exotherm that increased the temperature of the contents within the flask to 19° C. for a short time before the temperature returned to about 2°-3° C. The reaction mixture was removed from the ice bath and stirred until it reached room temperature. This mixture was poured into a Buchner funnel and filtered. The solid product, which had a brown appearance, was washed twice with generous amounts of water. The solid product (5-methoxy-2-nitrosophenol) was filtered and placed in a 40° C. oven overnight.

0.15 grams of the 5-methoxy-2-nitrosophenol and 0.33 grams of 1,2,3,3,4(and 6), 5-hexamethyl indolium iodide in about 25 milliliters of ethanol were refluxed in the presence of about 0.2 grams of piperidine for about three hours. The resulting product, an oil-like substance, was purified by flash column chromatography twice. Mass spectrometry, proton nuclear magnetic resonance (NMR) spectroscopy and infrared (IR) analysis was used to confirm that the product, 7-methoxy-1',3',3',4'(and 6'),5'-pentamethylspiro[2H-1,4-benzoxazine-2,2'-indoline], was produced. An ethanol solution of the product was colorless but changed to blue when irradiated with ultraviolet light. The solution returned to its original colorless condition after the ultraviolet light was removed.

EXAMPLE 2

In accordance with the method described in Example 1, 3.15 grams of 3,5-dimethoxyphenol was dissolved in 0.8 grams of sodium hydroxide in 100 milliliters of water. The solution was cooled in an ice bath and 1.38 grams of sodium nitrite was added to the solution. Sulfuric acid (2.5 grams) was added slowly to the reaction mixture while maintaining the mixture at temperatures of about 3°-4° C. Following addition of the sulfuric acid, the reaction mixture was allowed to warm to room temperature overnight. The product was filtered and washed with copious amounts of water. The solid product (3,5-dimethoxy-2-nitrosophenol) was dried in air.

Using the condensation method described in Example 1, 0.19 grams of 3,5-dimethoxy-2-nitrosophenol was condensed with 0.35 grams of 1,2,3,3,4(and 6),5-hexamethyl indolium iodide in ethanol in the presence of piperidine. The condensation product, 5,7-dimethoxy-1',3',3',4'(and 6'),5'-pentamethylspiro[2H-1,4-benzoxazine-2,2'indoline], an oily material, was purified by flash column chromatography. An ethanol solution of the material was colorless but changed to red when irradiated with ultraviolet light.

EXAMPLE 3

Using the condensation procedure of Example 1, 0.18 grams of 3,5-dimethoxy-2-nitrosophenol was condensed with 0.36 grams of 1,2,3,3-tetramethyl-5-methoxy indolium iodide in ethanol in the presence of piperidine. The product, 5,7-dimethoxy-1',3',3'-trimethyl-5'-methoxyspiro[2H-1,4-benzoxazine-2,2'indoline], an oily substance, was filtered through carbon black. An ethanol solution of the product was colorless but changed to pink when irradiated with ultraviolet light. The solution returned to its original colorless condition after the ultraviolet light was removed.

EXAMPLE 4

Utilizing the procedure of Example 2, 5 grams of 3-chloro-5-methoxy phenol was dissolved in 1.26 grams of sodium hydroxide in 100 milliliters of water. The solution was cooled in an ice bath and 2.18 grams of sodium nitrite added to the solution. Thereafter, 4 grams of sulfuric acid was added slowly to the reaction mixture while maintaining it at about 3°-4° C. After addition of all of the sulfuric acid, the reaction was allowed to warm to room temperature and the product filtered and washed with copious amounts of water. The washed product was first dried in air and then dried in a 70° C. vacuum oven.

0.18 grams of the dried product (2-nitroso-3-chloro-5-methoxy-phenol) was condensed with 0.32 grams of 1,2,3,3,4(and 6),5-hexamethyl indolium iodide in ethanol in the presence of piperidine. The product, 5-chloro-7-methoxy-1',3',3',4'(and 6'),5'-pentamethylspiro[2H-1,4-benzoxazine-2,2'-indoline], an oily substance, was filtered with carbon black. An ethanol solution of the product was colorless but changed to blue when irradiated with ultraviolet light. The solution returned to its original colorless condition after the ultraviolet light was removed. A toluene solution of the product changed to pink when irradiated with ultraviolet light. A hexane solution of the product changed to red when irradiated with ultraviolet light.

EXAMPLE 5

In 20 milliliters of glacial acetic acid was dissolved 6.96 grams of 4-nitrophenol (0.05 mole). The solution was diluted with 40 milliliters of water. The final solution was adjusted to a pH of about 4-4.5 with 47 grams of sodium acetate. In a second vessel, 4.78 grams of anhydrous copper sulfate (0.03 mole) and 5.18 grams of sodium nitrite (0.075 mole) were dissolved in 150 milliliters of water. The dark green copper sulfate-sodium nitrite reaction solution was gently added to the 4-nitrophenol solution while maintaining the solution pH in the 4-4.5 range with sodium acetate. Because no significant reaction was observed, a second copper sulfate-sodium nitrite solution was prepared and added to the reaction mixture. Subsequently, the reaction mixture was brought to boiling with vigorous stirring for 2-3 minutes and the resulting dark purple solution allowed to cool to room temperature. A small amount of powder was formed. The powder was collected, washed with water and methanol and dried in air. An almost black powder was obtained.

The aforesaid black powder (0.5 grams) was added slowly to a suspension of 1.0 grams of 1,2,3,3,4(and 6),5-hexamethyl indolium iodide in 30 milliliters of hot toluene over a period of about 5-10 minutes. The reaction was refluxed for about 10 minutes and filtered while hot. The filtrate was evaporated under vacuum at room temperature and allowed to dry overnight in the air. The powdered product was treated with 50 milliliters of boiling n-hexane four times. All of the n-hexane extracts were combined and evaporated under vacuum to a small volume (about 5-10 milliliters). A yellow-orange powder formed. This powder was collected, washed with fresh n-hexane and air-dried.

The resulting dried product was characterized by solution photochromicity, proton nuclear magnetic resonance (NMR) spectroscopy and mass spectrometry. The product forms a pale yellow solution in both ethanol and toluene. These solutions turn green when exposed to ultraviolet light radiation (366 manometers) and fade to the pale yellow color when kept in the dark. Characterization of the product by mass spectrometry indicated that a major component thereof corresponded to the compound: 6-nitro-1',3',3',4'(and 6'),5'-pentamethylspiro[2H-1,4-benzoxazine-2,2'-indoline]. A minor component of the product was found to be a material corresponding to: 6-nitro-2-benzyl-1',3',3',4'(and 6'),5'-pentamethylspiro[2H-1,4-benzoxazine-2,2'-indoline].

EXAMPLE 6

The procedure of Example 5 was followed except that 4-chlorophenol was substituted for the 4-nitrophenol in Example 5. 1.83 grams of the copper complex was added slowly to 3.29 grams of 1,2,3,3,4(and 6),5-hexamethyl indolium iodide suspended in 40 milliliters of absolute ethanol containing 1.1 grams of triethylamine. The copper complex was added while heating and stirring the suspension of the indolium iodide salt over 20-25 minutes. The resulting dark solution was refluxed for about three hours. The resulting reaction mixtures was allowed to cool to room temperature after which the liquid was evaporated. A dark (almost black) paste was obtained. Thin layer chromatography of the paste eluted with a methylene chloride:acetone solvent (in a ratio of 9:1) revealed the presence of a photochromic compound, e.g., 6-chloro-1',3',3',4'(and 6'),5'-pentamethylspiro[2H-1,4-benzoxazine-2,2'-indoline]. The photochromic compound changed from a pale yellow to blue under exposure to ultraviolet light.

EXAMPLE 7

Five grams of 3-fluoro-phenyl hydrazine and 5 milliliters of methyl isopropyl ketone were mixed in 45 milliliters of acetic acid and heated to 110° C. The reaction mixture was maintained at reaction temperature overnight (16 hours). The reaction mixture was diluted with diethyl ether and the resulting mixture washed three times with distilled water. The organic layer was neutralized with sodium carbonate, washed with a saturated sodium chloride solution and dried over anhydrous magnesium sulfate. 5.62 grams of product were recovered.

4.38 grams of the aforesaid reaction product was reacted with excess iodomethane at 40° C. for 3 hours. About 50 milliliters of hexane were added to the reaction mixture to form a slurry which was refluxed for 2 hours. The resulting solid crude product was washed with ethyl acetate and the washed solid dried. 5.86 grams of the Fischer's base, 1,2,3,3-tetramethyl-4(6)-fluoro-indolium iodide were recovered.

2.40 grams of the aforesaid iodo salt was condensed with 1.32 grams of 3,5-dimethoxy-2-nitrosophenol in ethanol with an excess of diisopropylamine at 70° C. for 5 hours. The product, 5,7-dimethoxy-1',3',3'-trimethyl-4'(and 6') fluoro spiro[2H-1,4-benzoxazine-2,2'-indoline], changed from a pale yellow to orange when exposed to ultraviolet light in hexane and ethanol. The solution returned to its original hue when the ultraviolet light was removed.

EXAMPLE 8

The procedure of Example 7 was used to prepare the following phtochromic spiro(indoline)benzoxazine compounds:
(a) 5,7-dimethoxy-1',3',3'-trimethyl-4'(and 6') chloro spiro 2H-1,4-benzoxazine-2,2'-indoline],
(b) 5,7-dimethoxy-1',3',3'-trimethyl-7'-chloro spiro[2H-1,4-benzoxazine-2,2'-indoline],
(c) 5,7-dimethoxy-1',3',3'-trimethyl-5'-chloro spiro[2H-1,4-benzoxazine-2,2'-indoline],
(d) 5,7-dimethoxy-1',3',3'-trimethyl-7'-fluoro spiro[2H-1,4-benzoxazine-2,2'-indoline],
(e) 5,7-dimethoxy-1',3',3'-trimethyl-4'(and 6') bromo spiro[2H-1,4-benzoxazine-2,2'-indoline],
(f) 5,7-dimethoxy-1',3',3'-trimethyl-5'-fluoro spiro [2H-1,4-benzoxazine-2,2'-indoline],
(g) 5-chloro-7-methoxy-1',3',3'-trimethyl-4'(and 6')-fluoro spiro [2H-1,4-benzoxazine-2,2'-indoline],
(h) 7-methoxy-1',3',3'-trimethyl-4'(and 6')-trifluoromethyl spiro [2H-1,4-benzoxazine-2,2'-indoline],
(i) 5,7-dimethoxy-1',3',3'-trimethyl-4'(and 6') trifluoromethyl spiro [2H-1,4-benzoxazine-2,2'-indoline], and
(j) 5-chloro-7-methoxy-1',3',3'-trimethyl-4'(and 6')-trifluoromethyl spiro [2H-1,4-benzoxazine-2,2'-indoline].

Although the present invention has been described with reference to specific details of certain embodiments thereof, it is not intended that such detail should be regarded as limitations upon the scope of the invention except as and to the extent that they are included in the accompanying claims.

We claim:
1. A photochromic article comprising a polymerized organic host material and a photochromic amount of a photochromic compound represented by the graphic formula:

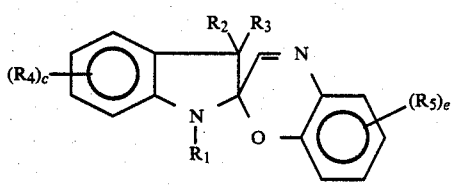

wherein:
(a) $R_1$ is selected from the group consisting of $C_1$–$C_8$ alkyl, phenyl, phen($C_1$–$C_4$)alkyl, naphth ($C_1$–$C_4$) alkyl, allyl, acrylyl, methacrylyl, $C_1$–$C_4$ acyloxy ($C_2$–$C_6$)alkyl, carboxy($C_2$–$C_6$)alkyl, cyano($C_2$–$C_6$)alkyl, hydroxy($C_2$–$C_6$)alkyl, $(C_2H_4O)_m \cdot CH_3$, and mono- and di-substituted phenyl, said phenyl substituents being selected from $C_1$–$C_4$ alkyl and $C_1$–$C_5$ alkoxy, and m is a number from 1 to 6;
(b) $R_2$ and $R_3$ are each selected from the group consisting of $C_1$–$C_5$ alkyl, phenyl, and mono- and di-substituted phenyl, benzyl or combine to form a cyclic ring selected from the group consisting of an alicyclic ring containing from 6 to 8 carbon atoms (including the spiro carbon atom), norbornyl and adamantyl, said phenyl substituents being selected from $C_1$–$C_4$ alkyl and $C_1$–$C_5$ alkoxy;
(c) each $R_4$ is selected from the group consisting of $C_1$–$C_5$ alkyl, halogen, $C_1$–$C_5$ alkoxy, nitro, cyano, $C_1$–$C_4$ monohaloalkyl, $C_1$–$C_4$ polyhaloalkyl, $C_1$–$C_8$ alkoxycarbonyl, and $C_1$–$C_4$ acyloxy;
(d) each $R_5$ is selected from the group consisting of halogen, $C_1$–$C_4$ alkyl, $C_1$–$C_5$ alkoxy, nitro, cyano, thiocyano, $C_1$–$C_4$ monohaloalkyl, and $C_1$–$C_2$ polyhaloalkyl; and
(e) the letters "c" and "e" are numbers of from 0 to 4 and 1 to 4 respectively,
said organic host material being selected from the group consisting of polymers of polyol(allyl carbonate), polyacrylates, poly(alkylacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethane, polycarbonate, poly(ethylene terephthalate), polystyrene, poly(styrene-methylmethacrylate)-copolymers, poly(styrene-acrylonitrile) copolymers, and poly(vinyl butyral).

2. The photochromic article of claim 1 wherein the polyol(allyl)carbonate is selected polymer from transparent poly and its copolymers with vinyl acetate.

3. The photochromic article of claim 1 wherein the photochromic compound is represented by the graphic formula:

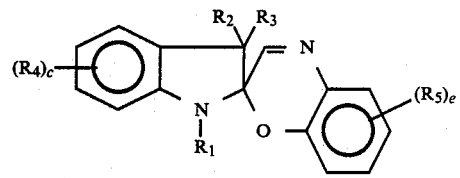

wherein:
(a) $R_1$ is selected from the group consisting of $C_1$–$C_4$ alkyl, phenyl, benzyl, naphth ($C_1$–$C_2$) alkyl, carboxy ($C_2$–$C_4$) alkyl, cyano ($C_2$–$C_4$) alkyl, $C_1$–$C_4$ acyloxy ($C_2$–$C_4$) alkyl, hydroxy ($C_2$–$C_4$) alkyl and $(C_2H_4O)_m \cdot CH_3$, wherein m is a number of from 1 to 3,
(b) $R_2$ and $R_3$ are each selected from $C_1$–$C_5$ alkyl,
(c) each $R_4$ is selected from the group consisting of $C_1$–$C_2$ alkyl, chloro, fluoro, $C_1$–$C_5$ alkoxy and $C_1$–$C_2$ trihaloalkyl,
(d) each $R_5$ is selected from the group consisting of chloro, fluoro, bromo, nitro, $C_1$–$C_4$ alkyl, $C_1$–$C_2$ alkoxy and trifluoromethyl, and
(e) the letter "c" is a number of from 0 to 2, and the letter "e" is a number of from 1 to 3.

4. A photochromic article comprising a solid transparent polymerized organic host material selected from the group consisting of polycarbonate, polymers of polyol (allyl carbonate), polymethylmethacrylate, cellulose acetate, cellulose acetate propionate, cellulose acetate butyrate, poly(vinyl acetate), poly(vinyl chloride), poly(vinylidene chloride), poly(ethylene terephthalate), poly(vinyl butyral), polystyrene, poly(styrenemethylmethacrylate)copolymer, and poly(styrene acrylonitrile)copolymer, said host material containing a photochromic amount of a photochromic compound represented by the graphic formula:

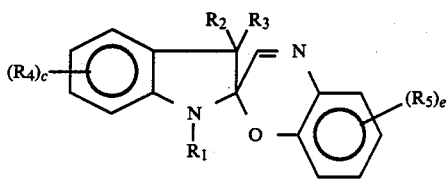

wherein:
(a) $R_1$ is selected from the group consisting of $C_1$–$C_4$ alkyl, phenyl, benzyl, 1-naphthylmethyl, B-carboxyethyl, B-cyanoethyl, acetoxyethyl, hydroxyethyl and $(C_2H_4O)_2 \cdot CH_3$,
(b) $R_2$ and $R_3$ are each selected from $C_1$–$C_5$ alkyl,
(c) each $R_4$ is selected from the group consisting of $C_1$–$C_2$ alkyl, chloro, fluoro, $C_1$–$C_5$ alkoxy and $C_1$–$C_2$ trihaloalkyl,
(d) each $R_5$ is selected from the group consisting of chloro, fluoro, bromo, nitro, $C_1$–$C_2$ alkyl, $C_1$–$C_2$ alkoxy and trifluoromethyl, and
(e) the letter "c" is a number of from 0 to 2, and the letter "e" is a number of from 1 to 3.

5. The photochromic article of claim 4 wherein $R_1$ is $C_1$–$C_4$ alkyl, $R_2$ and $R_3$ are each methyl or ethyl, each $R_4$ is trifluoromethyl, fluorine, chlorine, methyl, ethyl or methoxy, and each $R_5$ is trifluoromethyl, chloro, fluoro, methyl, ethyl, methoxy and ethoxy.

6. The photochromic article of claim 4 wherein the photochromic compound is present in amounts of from 0.05 to 10 weight percent.

7. The photochromic article of claim 6 wherein the polyol(allyl carbonate) polymer is selected from poly and its copolymers with vinyl acetate.

8. The photochromic article of claim 7 wherein the copolymer is from 80–90 weight percent diethylene glycol bis(allyl carbonate) and 10–20 weight percent vinyl acetate.

9. An article according to claim 1 wherein $R_1$ is a $C_1$–$C_4$ alkyl, $R_2$ and $R_3$ are each selected from the group consisting of methyl and ethyl, each $R_4$ is selected from the group consisting of methyl, ethyl, fluorine and trifluoromethyl, each $R_5$ is selected from the group consisting of $C_1$–$C_4$ alkyl, methoxy and ethoxy, the letter "c" is a number of from 0 to 2, and the letter "e" is a number of from 1 to 3.

10. An article according to claim 9 wherein each $R_5$ is methoxy and the letter "e" is 2.

11. An article according to claim 10 wherein the $R_5$ substituents are located at the 5 and 7 positions.

12. An article according to claim 9 wherein each $R_5$ substituent is selected from the group consisting of $C_1$–$C_4$ alkyl and methoxy and the letter "e" is 3.

13. An article according to claim 12 wherein the $R_5$ substituents are located at the 5, 7 and 8 positions.

14. An article according to claim 3 wherein $R_1$ is $C_1$–$C_4$ alkyl, $R_2$ and $R_3$ are each methyl or ethyl, each $R_4$ is chloro, fluoro, trifluoromethyl, methyl, ethyl or methoxy, each $R_5$ is chloro, fluoro, $C_1$–$C_4$ alkyl, methoxy or ethoxy, the letter "c" is 0 to 2 and the letter "e" is 1 to 3.

15. The photochromic article of claim 4 wherein the host material is a polymer prepared from diethylene glycol bis(allyl carbonate).

16. The photochromic article of claim 15 wherein $R_1$ is a $C_1$–$C_4$ alkyl, $R_2$ and $R_3$ are each selected from the group consisting of methyl and ethyl, each $R_4$ is selected from the group consisting of methyl, ethyl, fluorine and trifluoromethyl, each $R_5$ is selected from the group consisting of $C_1$–$C_4$ alkyl, methoxy and ethoxy, the letter "c" is a number of from 0 to 2, and the letter "e" is a number of from 1 to 3.

17. The photochromic article of claim 16 wherein each $R_5$ is methoxy and the letter "e" is 2.

18. The photochromic article of claim 17 wherein the $R_5$ substituents are located at the 5 and 7 positions.

19. The photochromic article of claim 16 wherein each $R_5$ substituent is selected from the group consisting of $C_1$–$C_4$ alkyl and methoxy and the letter "e" is 3.

20. The photochromic article of claim 19 wherein the $R_5$ substituents are located at the 5, 7 and 8 positions.

* * * * *

UNITED STATES PATENT AND TRADEMARK OFFICE
CERTIFICATE OF CORRECTION

PATENT NO. : 4,909,963
DATED : March 20, 1990
INVENTOR(S) : Won Suk Kwak and Chin-Wen Chen It is certified that error appears in the above-identified patent and that said Letters Patent is hereby corrected as shown below:

Claim 2, column 16, lines 39 and 40, "Polyol(allyl)carbonate is selected polymer from transparent poly" should be --polyol(allyl carbonate) polymer is selected from transparent poly[diethylene glycol bis(allyl carbonate)]--.

Claim 7, column 17, lines 47 and 48, "from poly" should be --from poly[diethylene glycol bis(allyl carbonate)]--.

Signed and Sealed this

Twenty-third Day of April, 1991

Attest:

HARRY F. MANBECK, JR.

*Attesting Officer*     *Commissioner of Patents and Trademarks*